(12) United States Patent
Kawakami et al.

(10) Patent No.: US 7,959,655 B2
(45) Date of Patent: Jun. 14, 2011

(54) SELF-ALIGNING ATTACHMENT DEVICES AND METHODS FOR ATTACHING AN ELONGATED MEMBER TO A VERTEBRAL MEMBER

(75) Inventors: Noriaki Kawakami, Achi (JP); Jaredan Braal, Memphis, TN (US); Roy Lim, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1132 days.

(21) Appl. No.: 11/682,528

(22) Filed: Mar. 6, 2007

(65) Prior Publication Data
US 2008/0234745 A1 Sep. 25, 2008

(51) Int. Cl.
*A61B 17/70* (2006.01)
(52) U.S. Cl. .......................... 606/276; 606/246; 606/278
(58) Field of Classification Search .......... 606/276–278, 606/60, 246, 264, 265
See application file for complete search history.

(56) References Cited

U.S. PATENT DOCUMENTS

| | | |
|---|---|---|
| 5,261,909 A | 11/1993 | Sutterlin et al. |
| 5,281,222 A | 1/1994 | Allard et al. |
| 5,380,326 A | 1/1995 | Lin |
| 5,545,167 A | 8/1996 | Lin |
| 5,578,033 A | 11/1996 | Errico et al. |
| 5,584,832 A | 12/1996 | Schlapfer |
| 5,609,593 A | 3/1997 | Errico et al. |
| 5,609,594 A | 3/1997 | Errico et al. |
| 5,611,800 A | 3/1997 | Davis et al. |
| 5,634,925 A | 6/1997 | Urbanski |
| 5,643,264 A | 7/1997 | Sherman et al. |
| 5,645,544 A | 7/1997 | Tai et al. |
| 5,662,653 A | 9/1997 | Songer et al. |
| 5,676,665 A | 10/1997 | Bryan |
| 5,688,273 A | 11/1997 | Errico et al. |
| 5,688,274 A | 11/1997 | Errico et al. |
| 5,740,254 A | 4/1998 | Thompson et al. |
| 5,741,254 A | 4/1998 | Henry et al. |
| 5,785,711 A | 7/1998 | Errico et al. |
| 5,810,818 A | 9/1998 | Errico et al. |
| 5,961,518 A | 10/1999 | Errico et al. |
| 5,976,135 A | 11/1999 | Sherman et al. |
| 6,017,344 A | 1/2000 | Errico et al. |
| 6,352,537 B1 | 3/2002 | Strnad |
| 6,610,063 B2 | 8/2003 | Kumar et al. |
| 6,648,887 B2 | 11/2003 | Ashman |
| 6,749,361 B2 | 6/2004 | Hermann et al. |
| 6,911,030 B1 | 6/2005 | Vanacker et al. |
| 2002/0169450 A1 | 11/2002 | Lange |
| 2003/0139745 A1 | 7/2003 | Ashman |

(Continued)

FOREIGN PATENT DOCUMENTS
JP          2000037404    *  2/2000

*Primary Examiner* — Eduardo C Robert
*Assistant Examiner* — Ellen C Hammond

(57) ABSTRACT

The present application is directed to a device for connecting an elongated member within a patient. The device includes a body with a receiving section to receive the elongated member, and an engagement section to engage a support structure, such as a vertebral member. The receiving section is sized to receive the elongated member in a first orientation. The process of securing the elongated member within the receiving section causes the device to pivot about the elongated member to a second orientation. This pivoting motion causes the engagement section to more securely attach to the support structure.

17 Claims, 3 Drawing Sheets

U.S. PATENT DOCUMENTS

| | | | |
|---|---|---|---|
| 2003/0144664 A1* | 7/2003 | Cavagna et al. | 606/61 |
| 2003/0149432 A1 | 8/2003 | Frigg et al. | |
| 2005/0080414 A1* | 4/2005 | Keyer et al. | 606/61 |
| 2005/0113835 A1 | 5/2005 | Ashman | |
| 2006/0089643 A1 | 4/2006 | Mujwid | |
| 2006/0116677 A1 | 6/2006 | Burd et al. | |

* cited by examiner

SELF-ALIGNING ATTACHMENT DEVICES AND METHODS FOR ATTACHING AN ELONGATED MEMBER TO A VERTEBRAL MEMBER

BACKGROUND

The present application is directed to self-aligning attachment devices and methods of use and, more particularly, to devices that pivot from a first orientation to receive an elongated member to a second orientation that captures the elongated member and secures the device to a vertebral member.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Various conditions may lead to damage of the vertebral members and/or intervertebral discs. The damage may result from a variety of causes including a specific event such as trauma, a degenerative condition, a tumor, or infection. Damage to the intervertebral discs and vertebral members can lead to pain, neurological deficit, and/or loss of motion. Elongated members, such as but not limited to rods, bars, and blades, may extend along the spine to redistribute stresses and/or restore proper alignment of the vertebral members. The elongated members may be substantially straight, or include a curved configuration to conform to the curvature of the spine.

The elongated members should be securely fixed to one or more of the vertebral members. Fixation often proves difficult because of the varied shape and dimensions of the vertebral members.

SUMMARY

The present application is directed to self-aligning attachment devices and methods of use. The device may include a body with a receiving section and an engagement section. The receiving section is sized to receive an elongated member. The engagement section is constructed to engage a support structure for attaching the device. One method of use includes initially positioning the elongated member within the receiving section while the device is in a first orientation. The elongated member is then secured within the receiving section that causes the body to pivot to the second orientation. This pivoting motion causes the engagement member to more securely engage the support structure.

DETAILED DESCRIPTION

The present application is directed to devices and methods for connecting an elongated member within a patient. The device includes a body with a receiving section to receive the elongated member, and an engagement section to engage a support structure, such as a vertebral member. The receiving section is sized to receive the elongated member in a first orientation. The process of securing the elongated member within the receiving section causes the device to pivot about the elongated member to a second orientation. This pivoting motion causes the engagement section to more securely attach to the support structure.

Figure 1:
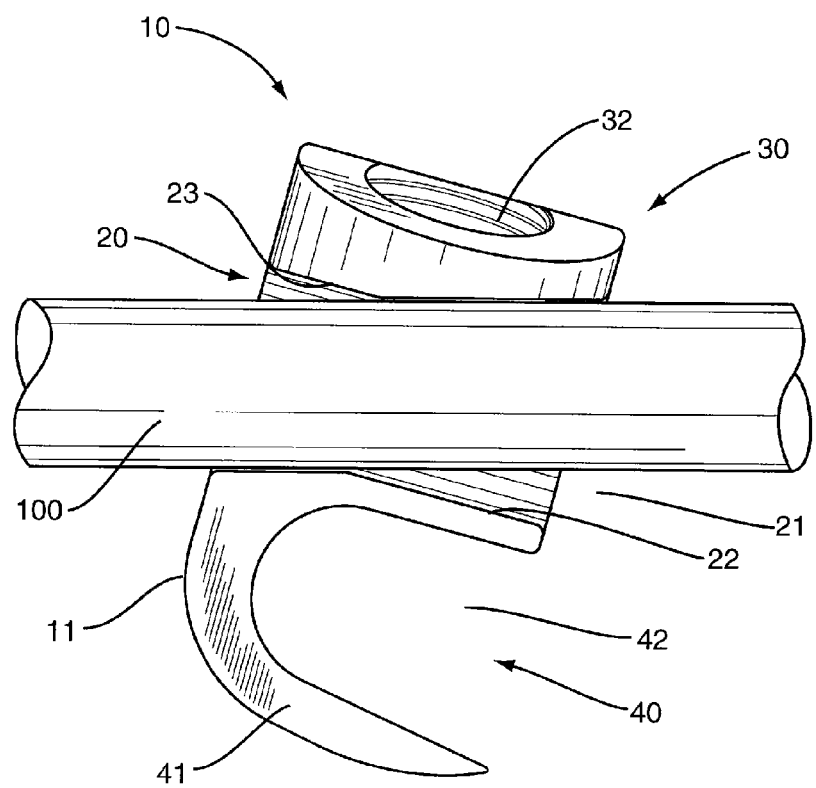
FIG. 1 is a front view of the device in a first orientation relative to an elongated member according to one embodiment.
Figure 2:
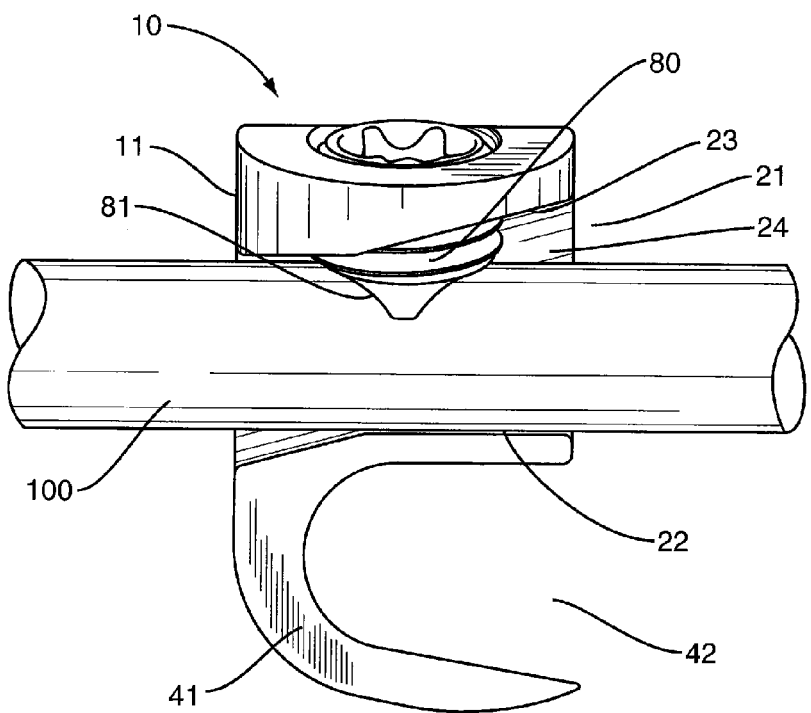
FIG. 2 is a front view of the device in a second orientation relative to the elongated member according to one embodiment.

FIGS. 1 and 2 illustrate one embodiment of the device 10. FIG. 1 illustrates the device 10 in the first orientation, and FIG. 2 illustrates the device 10 in the second orientation. Device 10 generally includes a receiving section 20 to receive the elongated member 100, a clamping section 30 to secure the elongated member 100, and an engagement section 40 to secure the device 10 to a support structure within the patient.

In this embodiment, the device 10 includes a body 11 of a solid, unitary construction. Body 11 may be formed of a variety of materials, including metals suitable for surgical implants such as stainless steel, titanium, nickel titanium, cobalt chromium, bone, ceramics, or composite materials such as carbon fiber. In other embodiments, body 11 is constructed of separate sections that are connected together.

The receiving section 20 includes an opening 21 that includes a lower side 22, upper side 23, and rear side 24. The lower side 22 includes a first section 25 and a second section 26 aligned at different angles and meet at a corner 53. The upper side 23 includes first and second sections 28, 29 that meet at corner 54. The first section 25 of the lower side 22 and second section 29 of the upper side 23 may be substantially parallel. Further, the second section 26 of the lower side 22 and first section 28 of the upper side 23 may be substantially parallel.

Receiving section 20 may be further defined to include two separate tapered sections that extend inward from opposing sides. A first tapered section is formed by sides 28 and 25 and extends into the body 11 from a first side. A second tapered section is formed by sides 29, 26 and extends into the body 11 from a second opposite side. The tapered sections meet along a line that extends between corners 53, 54.

Figure 3:
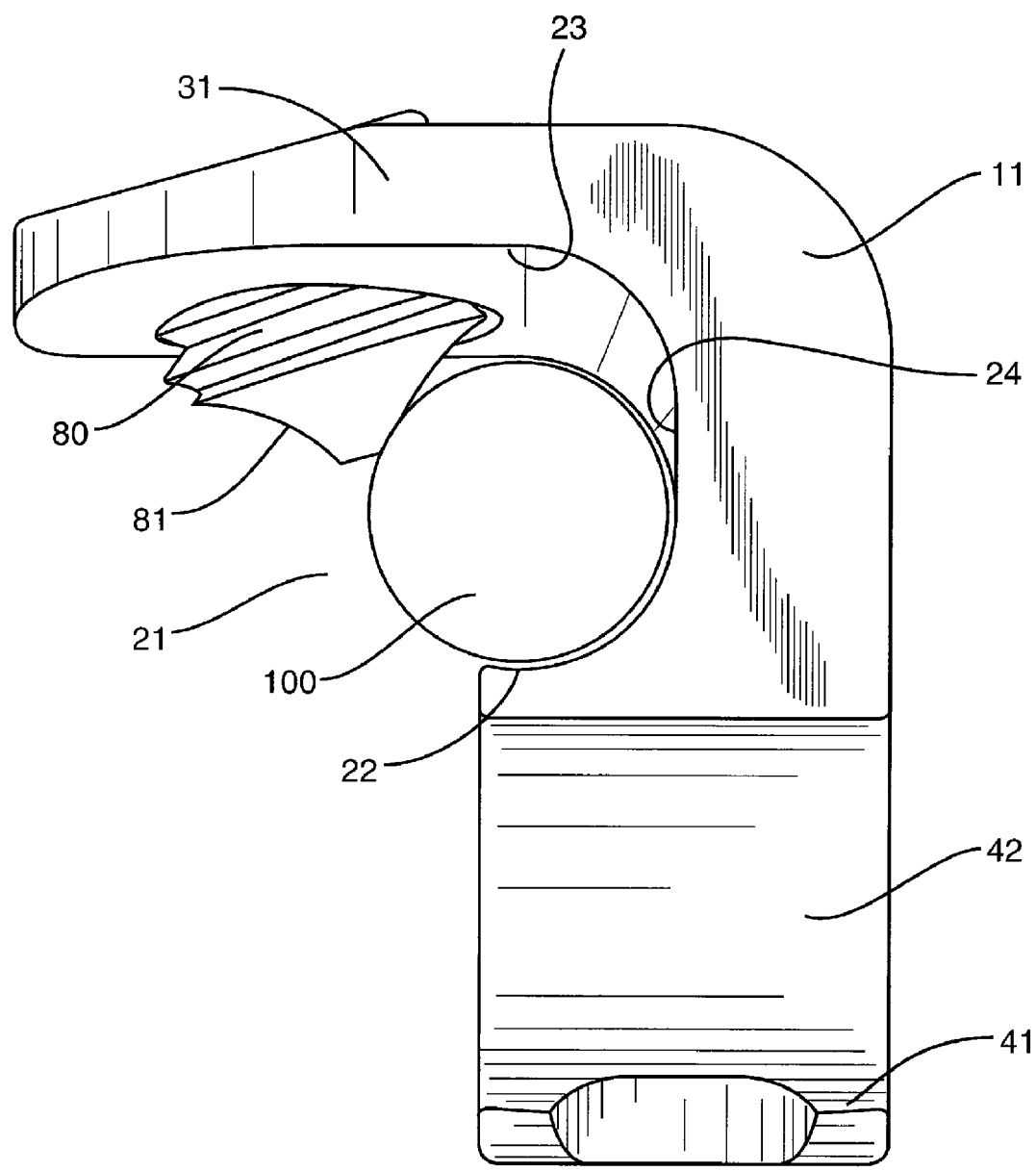
FIG. 3 is a side view of the device and an elongated member according to one embodiment.
Figure 4:
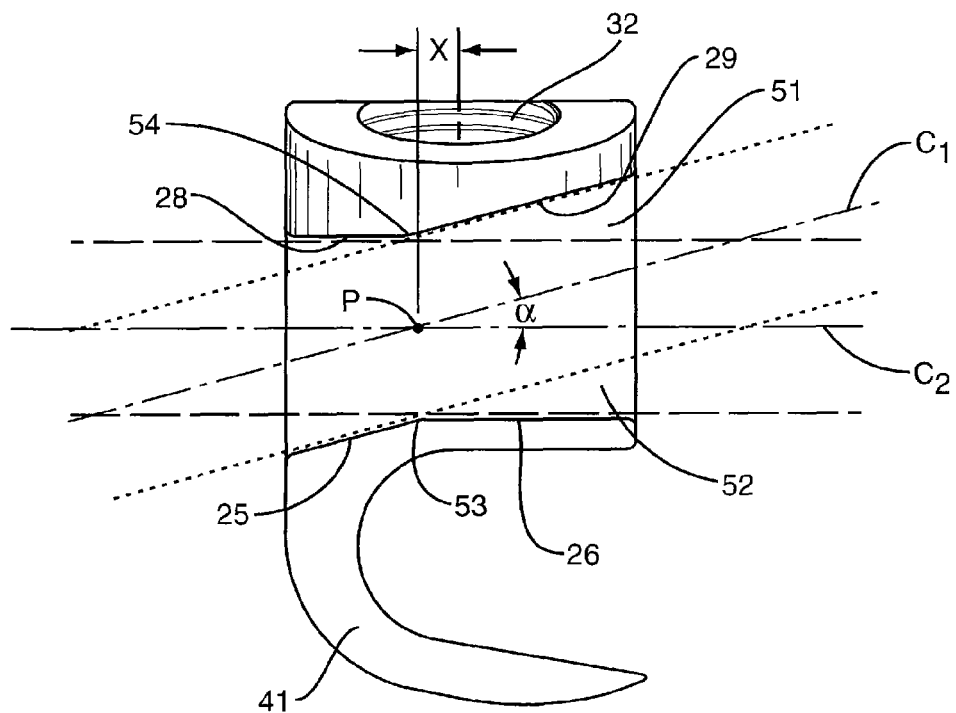
FIG. 4 is a schematic view of the device illustrating first and second channels according to one embodiment.

The opening 21 is positioned on a side of the body 11 for side-loading of the elongated member 100. The receiving section 20 is a continuous space sized to maintain and allow for the elongated member 100 to move between the first and second orientations. As illustrated in FIG. 3, the rear side 24 is substantially flat to allow the body 11 to pivot between orientations. As illustrated in FIG. 4, opening 21 may functionally include a first channel 51 with a centerline C1, and a second channel 52 with a centerline C2. First channel 51 is formed by the first section 25 and the second section 29. The second channel 52 is formed by the first section 28 and second section 26. The channels 51, 52 are positioned in an overlapping arrangement. The centerlines C1, C2 intersect at point P.

The amount of pivoting movement between the first and second orientations is defined by the angle α formed between the centerlines C1, C2. In one embodiment, angle α is in a range of between about 15° and about 40°. The amount of pivoting movement may include the entire range of motion defined by angle α, or may be some amount less than α. By way of example, the size of the receiving section 20 may allow for pivoting up to 40° but the engagement section 40 is fully engaged upon movement of 30°. Therefore, it is unnecessary for the device 10 to pivot the remaining 10°.

Clamping section 30 functions to clamp the elongated member 100 within the receiving section 20. Clamping section 30 includes an arm 31 that extends over the top of the receiving section. An aperture 32 extends through the arm 31 and opens into the receiving section. As illustrated in FIG. 3, arm 31 includes a length greater than a width of the elongated member 100. The aperture 32 is positioned towards an end of the arm 31 to be offset from the elongated member 100. Aperture 32 may further be angled towards the elongated member 100.

A fastener 80 is sized to fit within the aperture 32 and contact the elongated member 100. In one embodiment, fastener 80 is a screw with a threaded exterior that mates with threads in the aperture 32. Fastener 80 includes a tip 81 that contacts the elongated member 100. In one embodiment as illustrated in FIGS. 2 and 3, tip 81 includes a scalloped shape that roughly conforms to the shape of the elongated member 100. This increases the contact area between the fastener 80 and the elongated member 100. Because the aperture 32 is offset, the fastener 80 forces the elongated member 100 against the rear side 24. In another embodiment (not illustrated), the aperture 32 is aligned with the elongated member 100 (i.e., not offset) and the fastener 80 forces the member 100 against the lower side 22.

The engagement section 40 secures the body 11 to a support structure. Section 40 may include an arm 41 that is curved to form an opening 42 sized to receive the support structure. The support structure may include a lamina or transverse process of a vertebral member with the elongated member 100 sized to extend along the spine.

One method of use comprises initially engaging the engagement section 40 a first amount with the support structure. This places the body 11 in the first orientation. After the initial placement, the elongated member 100 is side-loaded into the receiving section 20. Specifically, the elongated member 100 is positioned within the first channel 51 as illustrated in FIG. 1.

The fastener 80 is then inserted through the aperture 32 in the clamping section 30 and into contact with the elongated member 100. Further tightening of the fastener 80 causes the body 11 to pivot relative to the elongated member 100. The extent of pivoting is controlled once the elongated member 100 moves into the second channel 52 and contacts sides 26, 28 of the receiving section 20 as illustrated in FIG. 2. This pivoting motion causes the arm 41 of the engagement section 40 to further move relative to the support structure for a more secure engagement.

Figure 5:
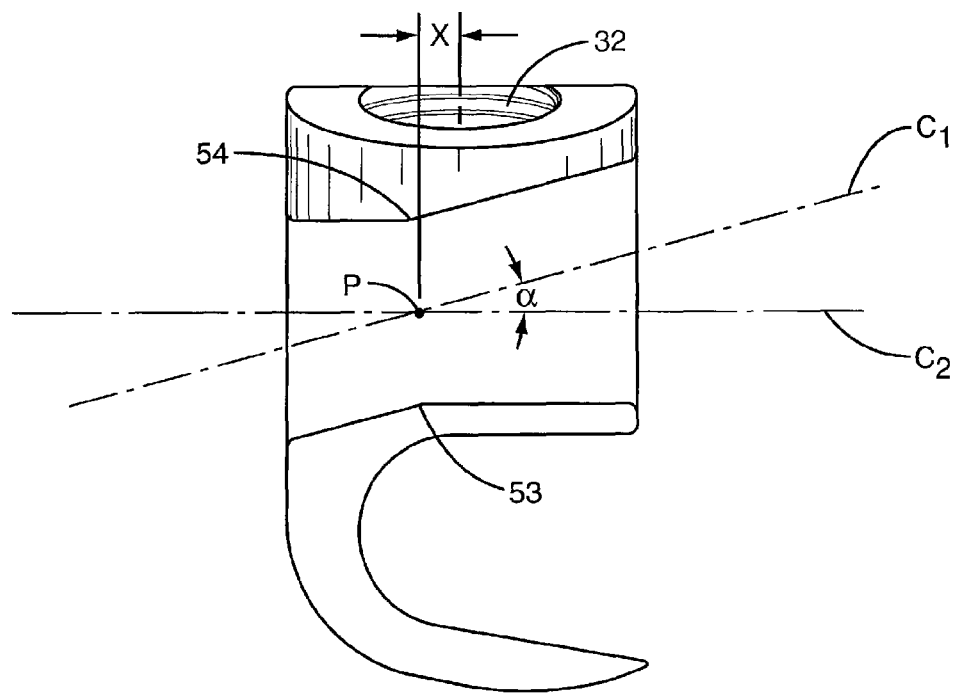
FIG. 5 is a schematic view of the device illustrating a distance X according to one embodiment.

The amount of pivoting force applied to the body 11 is based upon an offset X as illustrated in FIG. 5. Offset X is the distance between point P that is the intersection of centerlines C1, C2 and a center of the aperture 32. The greater the distance X, the greater the amount of force applied to the body 11 when moving between the first and second orientations. Likewise, a smaller distance X results in a smaller pivoting force. In one embodiment, the corners 53, 54 are aligned along a line with point P.

In one embodiment, the distance X is zero with the center of aperture 32 aligned with the point P. This requires that a pivoting force be applied in another manner because the contact of the fastener 80 with the elongated member 100 produces no force.

The elongated member 100 may include a variety of different shapes and sizes. In the embodiment of FIGS. 1, 2, and 3, member 100 is a rod with a substantially circular cross-sectional shape. Member 100 may also include but are not limited to rods of other cross-sectional shapes, cables, bars, and blades. The elongated member 100 may be substantially straight or curved.

In one embodiment, the device 10 attaches a vertebral rod to a vertebral member. The engagement section 40 is sized to engage with the vertebral member. In specific embodiments, the engagement section 40 is sized to engage the lamina or transverse processes of the vertebral member. The receiving section 20 is positioned to receive the vertebral rod that extends along the spine. The device 10 may be shapes and sized to attach to a vertebral member within the various regions of the spine, including the cervical, thoracic, lumbar and/or sacral regions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device for connecting an elongated member to a vertebral member, the device comprising:
   a receiving section including a first channel and a second channel in an overlapping arrangement and being aligned at angles to intersect at a first point, each of the channels sized to receive the elongated member, the receiving section includes a first tapering section that extends inward from a first side and a second tapering section that extends inward from a second opposite side; and
   a clamping section including an aperture that leads into the receiving section and is offset from the first point;
   insertion of a fastener into the aperture and against the elongated member causes the device to pivot from a first orientation with the elongated member in the first channel to a second orientation with the elongated member in the second channel.

2. The device of claim 1, wherein the receiving section includes opposing first and second sides each with first and second sections aligned at angles that form corners, the corners being aligned along a straight line with the first point.

3. The device of claim 1, wherein the first and second tapering sections meet along a straight line.

4. The device of claim 1 wherein the first channel is formed by a first wall of the first tapering section and a second opposing wall of the second tapering section.

5. The device of claim 1, wherein the receiving section comprises a substantially flat rear side.

6. The device of claim 1, wherein the aperture is positioned outward from a rear side of the receiving section and is aligned at an angle directed towards one of the first and second channels.

7. The device of claim 1, further comprising a hook positioned on an opposite side of the receiving section from the clamping section, the hook including an arm that forms an opening.

8. The device of claim 1, wherein the receiving section and the clamping section are constructed as a solid, unitary body.

9. The device of claim 1, wherein the first and second channels are aligned at an angle between the range of about 15° and about 40°.

10. A device for connecting an elongated member to a vertebral member, the device comprising:
   a receiving section including a first channel and a second channel in an overlapping arrangement and being aligned at angles with centerlines of each channel intersecting at a first point, each of the channels sized to receive the elongated member;
   a clamping section including an aperture leading into the receiving section, the aperture having a longitudinal axis extending through a center thereof, the first point being offset from the longitudinal axis;
   an engagement section including an opening to engage with the vertebral member;
   insertion of a fastener into the receiving section and against the elongated member at a point offset from the first point causes the device to pivot from a first orientation with the elongated member in the first channel and the engagement member engaging the vertebral member a first amount, to a second orientation with the elongated member in the second channel and the engagement member engaging the vertebral member a second greater amount.

11. The device of claim 10, wherein the receiving section and the engagement section are constructed as a solid, unitary body.

12. A device for connecting an elongated member to a vertebral member, the device comprising:
   a body including a receiving section, a clamping section, and an engaging section;
   the receiving section including a first channel and a second channel in an overlapping arrangement and being aligned at angles with centerlines of each channel intersecting at a first point and extending in a first plane, each of the channels sized to receive the elongated member;
   the clamping section having an aperture extending into the receiving section, the aperture having a longitudinal axis that extends through a center of the aperture and through the receiving section;
   the first point being offset from the longitudinal axis; and
   the engaging section to engage the vertebral member;
   insertion of a fastener into the receiving section causes the body to pivot within the first plane from a first orientation with the elongated member in the first channel and the engaging section engaging the vertebral member a first amount, to a second orientation with the elongated member in the second channel and the engaging section engaging the vertebral member a second greater amount.

13. The device of claim 12, wherein the receiving section includes a first tapering section that extends inward from a first side and a second tapering section that extends inward from a second opposite side.

14. The device of claim 12, wherein the receiving section and the engaging section are constructed as a solid, unitary body.

15. The device of claim 12, wherein the first and second channels are aligned at an angle between the range of about 15° and about 40°.

16. A device for connecting an elongated member to a vertebral member, the device comprising:
   a body including a receiving section, a clamping section positioned on a first side of the receiving section, and an engaging section positioned on a second side of the receiving section opposite from the clamping section;
   the receiving section including a side-loading channel including a first tapered section that extends inward from a first side and a second tapered section that extends inward from a second side, the first and second tapered sections intersecting along a line, the tapered sections extend different lengths into the receiving section;
   insertion of a fastener through the clamping section and against the elongated member at a point offset from the line causes the body to pivot about the elongated member to engage the engaging section with the vertebral member.

17. The device of claim 16, wherein the body includes a solid, unitary construction.

\* \* \* \* \*